United States Patent [19]
Wass

[11] Patent Number: 6,126,680
[45] Date of Patent: Oct. 3, 2000

[54] SELECTIVE CONVECTIVE BRAIN COOLING APPARATUS AND METHOD

[75] Inventor: C. Thomas Wass, Rochester, Minn.

[73] Assignee: Mayo Foundation for Medical Education and Research, Rochester, Minn.

[21] Appl. No.: 09/054,608

[22] Filed: Apr. 3, 1998

Related U.S. Application Data

[60] Provisional application No. 60/042,931, Apr. 3, 1997.

[51] Int. Cl.⁷ ........................................................ A61F 7/00
[52] U.S. Cl. ............................ 607/96; 607/107; 62/259.3
[58] Field of Search ..................... 607/96, 104, 107–109, 607/110, 112; 514/263, 269; 604/113, 500; 128/898

[56] References Cited

U.S. PATENT DOCUMENTS

| | | | |
|---|---|---|---|
| 4,753,242 | 6/1988 | Saggers . | |
| 5,261,399 | 11/1993 | Klatz et al. | 607/104 |
| 5,342,411 | 8/1994 | Maxted et al. | 607/107 |
| 5,603,728 | 2/1997 | Pachys | 607/110 |
| 5,860,292 | 1/1999 | Augustine et al. | 62/259.3 |

OTHER PUBLICATIONS

David B. Pryor et al., "The Changing survival benefits of coronary revascularization over time," *Circulation*, vol. 76 (suppl V), Nov. 1987, pp. V–13 to V–21.

Stephen Sloghoff, MD et al., "Etiologic Factors in Neuropsychiatric Complications Associated with Cardiopulmonary Bypass," *Anesthesia and Analgesia*, vol. 61, No. 11, Nov. 1982, pp. 903–911.

Nancy A. Nussmeier, MD et al., "Neuropsychiatric Complications after Cardiopulmonary Bypass: Cerebral Protection by a Barbiturate," *Anesthesiology*, vol. 64, 1986, pp. 165–170.

Judith A. Savageau, M.P.H. et al., "Neuropsychological dysfunction following elective cardiac operation–early assessment," *The Journal of Thoracic and Cardiovascular Surgery*, vol. 84, No. 4, Oct. 1982, pp. 585–594.

Anthony C. Breuer, MD et al., "Central Nervous System Complications of Coronary Artery Bypass Graft Surgery: Prospective Analysis of 421 Patients," *Stroke*, vol. 14, No. 5, 1983, pp. 682–687.

Abstract: T.A. Hammeke and J.E. Hastings, "Neuropsychologic alterations after cardiac operation", *J. Thoracic & Cardio. Surg.*, vol. 96, No. 2, Aug. 1988, pp. 326–331.

Stephen A. Mills, MD, "Cerebral Injury and Cardiac Operations," *Ann Thorac Surg*, 1993, vol. 56, pp. S86–S91.

M.S. Albin, MD et al., "Aeric Microemboli and the Transcranial Doppler (TCD): Episodic Frequency and Timing in 62 Cases of Open Heart Surgery," *Anesthesiology*, vol. 75, No. 3A, Sep. 1991, p. A53.

(List continued on next page.)

*Primary Examiner*—Linda C. M. Dvorak
*Assistant Examiner*—Roy Gibson
*Attorney, Agent, or Firm*—Fish & Richardson P.C.P.A.

[57] ABSTRACT

A method and apparatus for convective cooling of a brain in which cooled air is passed over a patient's head resulting in convective cooling of the patient's brain. The convective brain cooling apparatus comprises an air diffusing coverlet adapted to interface with an air cooling device and a coverlet capable of surrounding the patient's head and/or neck region. The method may also include the additional step of selectively controlling cerebral blood flow and/or cerebral metabolism to further cool the brain or to maintain the brain in a hypothermic state relative to the patent's core temperature. In alternative embodiments the apparatus and method may also include a cooling head cushion, an oral pharyngeal cooling device, a cool water misting device or the use of a network of elastic capillaries placed around the head or neck to maintain or increase the magnitude of the temperature gradient between the brain and the patient's body core.

29 Claims, 5 Drawing Sheets

OTHER PUBLICATIONS

W. Pugsley, FRCS et al., "The impact of Microemboli During Cardiopulmonary Bypass on Neuropsychological Functioning," *Stroke*, vol. 25, No. 7, Jul. 1994, pp. 1393–1399.

Richard E. Clark, MD et al., "Microemboli during coronary artery bypass grafting: Genesis and effect on outcome," *The Journal of Thoracic and Cardiovascular Surgery*, vol. 109, No. 2, pp. 249–258, 1995.

Gerald D. Silverberg, M.D., et al., "Hypothermia and cardiac arrest in the treatment of giant aneurysms of the cerebral circulation and hemangioblastoma of the medulla," *J. Neurosurg.*, vol. 55, Sep., 1981, pp. 337–346.

J. Tharion, M.S., M.Ch. et al., "Profound hypothermia with circulatory arrest," *The Journal of Thoracic and Cardiovascular Surgery*, vol. 84, No. 1, Jul., 1982, pp. 66–72.

William J. Greeley, M.D., et al. The effect of hypothermic cardiopulmonary bypass and total circulatory arrest on cerebral metabolism in neonates, infants, and children, *The Journal of Thoracic and Cardiovascular Surgery*, vol. 101, No. 5, May 1991, pp. 783–794.

JoAnne E. Natale, PhD., and Louis G. D'Alecy, DMD, PhD., "Protection From Cerebral Ischemia by Brain Cooling Without Reduced Lactate Accumulation in Dogs," *Stroke*, vol. 20, No. 6, Jun. 1989, pp. 770–777.

Hiroaki Minamisawa, MD et al., "The Effect of Mild Hyperthermia and Hypothermia on Brain Damage Following 5, 10, and 15 Minutes of Forebrain Ischemia," *Annals of Neurology*, vol. 28, No. 1, Jul. 1990, pp. 26–33.

Raul Busto et al., "Small Differences in Intraischemic Brain Temperature Critically Determine the Extent of Ischemic Neuronal Injury," *Journal of Cerebral Blood Flow and Metabolism*, vol. 7, No. 6, 1987, pp. 729–738.

Hiroaki Minamisawa et al., "The influence of Mild Body and Brain Hypothermia on Ischemic Brain Damage," *Journal of Cerebral Blood Flow and Metabolism*, vol. 10, No. 3, 1990, pp. 365–374.

David S. Warner et al., "Sevoflurane and Halothane Reduce Focal Ischemic Brain Damage in the Rat," *Anesthesiology*, vol. 79, No. 5, No. 1993, pp. 985–992.

M. Chopp, PhD, K.M.A. et al., "Effect of Mild Hyperthermia on Recovery of Metabolic Function After Global Cerebral Ischemia in Cats," *Stroke*, vol. 19, No. 12, Dec. 1988, pp. 1521–1525.

Qun Chen et al., "Temperature Modulation of Cerebral Depolarization During Focal Cerebral Ischemia in Rats: Correlation with Ischemic Injury," *Journal of Cerebral Blood Flow and Metabolism*, vol. 13, No. 3, 1993, pp. 389–394.

M.A. Baker et al., "Thermal relationship between tympanic membrane and hypothalamus in conscious cat and monkey," *Journal of Applied Physiology*, vol. 32, No. 6, Jun. 1972, pp. 739–742.

James N. Hayward and Mary Ann Baker, "Role of Cerebral arterial blood in the regulation of brain temperature in the monkey," *American Journal of Physiology*, vol. 215, No. 2, Aug. 1968, pp. 389–403.

J.D. Whitby and L.J. Dunkin, "Cerebral, Oesophageal and Nasopharyngeal Temperatures," *British Journal of Anaesthesia*, vol. 43, 1971, pp. 673–676.

K. Shiraki et al., "Independence of brain and tympanic temperatures in an unanesthetized human," *Journal of Applied Physiology*, 1988, vol. 65, pp. 482–486.

J. Gilbert Stone, M.D., et al., "Do Standard Monitoring Sites Reflect True Brain Temperature When Profound Hypothermia Is Rapidly Induced and Reversed?", *Anesthesiology*, vol. 82, No. 2, Feb. 1995, pp. 344–351.

Hiroaki Minamisawa, M.D. et al., "Preservation of Brain Temperature During Ischemia in Rats," *Stroke*, vol. 21, No. 5, May 1990, pp. 758–764.

Joseph S. Coselli, M.D. et al., "Determination of Brain Temperatures for Safe Circulatory Arrest during Cardiovascular Operation," *The Annals of Thoracic Surgery*, vol. 45, No. 6, Jun. 1988, pp. 638–642.

Brian P. Kavanagh, MB, BCh, BSc, MRCPI et al., "Effect of Warm Heart Surgery on Perioperative Management of Patients Undergoing Urgent Cardiac Surgery," *Journal of Cardiothoracic and Vascular Anesthesia*, vol. 6, No. 2 Apr. 1992, pp. 127–131.

Thomas D. Martin, M.D. et al., "Prospective, Randomized Trial of Retrograde Warm Blood Cardioplegia: Myocardial Benefit and Neurologic Threat," *Analogs of Thoracic Surgery*, 1994, vol. 57, pp. 298–304.

Hartzell V. Schaff, M.D. et al., "Regional Ischemia Distal to a Critical Coronary Stenosis During Prolonged Fibrillation– Improvement with Pulsatile Perfusion," *Cardiovascular Surgery*, 1976, Supp. 2, Circulation, vol. 56, No. 3, Sep., 1977, pp. II–25–II–32.

Timothy J. Gardner, M.D. et al., Stroke Following Coronary Artery Bypass Grafting: A Ten–Year Study, *The Annals of Thoracic Surgery*, vol. 40, No. 6, Dec., 1985, pp. 574–581.

Delos M. Cosgrove M.D. et al., "Primary myocardial revascularization," *The Journal of Thoracic and Cardiovascular Surgery*, vol. 88, No. 5, Part 1, Nov., 1984, pp. 673–684.

Nancy A. Nussmeier, M.D., "Adverse Neurologic Events: Risks of Intracardiac Versus Extracardiac Surgery," *Journal of Cardiothoracic and Vascular Anesthesia*, vol. 10, No. 1, Jan., 1996, pp. 31–37.

David A. Stump, PhD. et al., "Cerebral Emboli and Cognitive Outcome After Cardiac Surgery," *Journal of Cardiothoracic and Vascular Anesthesia*, vol. 10, No. 1, Jan. 1996, pp. 113–119.

Narda D. Croughwell, C.R.N.A. et al., "Jugular Bulb Saturation and Mixed Venous Saturation During Cardiopulmonary Bypass," *The Journal of Thoracic and Cardiovascular Surgery*, 1995, vol. 10 (Suppl.) pp. 503–508.

C. Michael Crowder, M.D., Ph.D., et al. "Jugular bulb temperature: comparison with brain surface and core temperatures in neurosurgical patients during mild hypothermia," vol. 85, Jul. 1996, pp. 98–103.

Robert L. McCauley et al., "Frostbite and Other Cold–Induced Injuries," *Wilderness Medicine*, 1995, pp. 129–145.

Andrea Kurz, M.D., et al., Thermoregulatory Vasoconstriction Impairs Active Core Cooling, *Anesthesiology*, vol. 82, No. 4., Apr. 1995, pp. 870–876.

William Fitch, "Brain Metabolism, *Anesthesia and Neurosurgery,*" Edited by Cottrell JE, Smith DS, St. Louis, Moseby–Year Book, Inc., 1994, pp. 1–16.

C. Thomas Wass, M.D., et al., "Anesthetic Technique Influences Brain Temperature During Cardiopulmonary Bypass in Dogs," *Ann. Thoracic Surgeons*, vol. 65, 1998, pp. 454–460.

C. Thomas Wass, M.D. and William L. Lanier, M.D., "Hypothermia–associated Protection from Ischemic Brain Injury: Implications for Patient Management," *Reprinted from International Anesthesiology Clinics*, vol. 34, No. 4, Fall 1996, pp. 95–111.

John D. Michenfelder and James H. Milde, "The Effect of Profound Levels of Hypothermia (Below 14° C) on Canine Cerebral Metabolism," *Journal of Cerebral Blood Flow and Metabolism*, vol. 12, No. 5, 1992, pp. 877–880.

David J. Cook M.D. et al., "A prospective, randomized comparison of cerebral venous oxygen saturation during normothermic and hypothermic cardiopulmonary bypass," *The Journal of Thoracic and Cardiovascular Surgery*, vol. 107, No. 4, Apr. 1994, pp. 1020–1029.

C. Thomas Wass, M.D., et al., "Temperature Changes of $\geq$° C) Alter Functional Neurologic Outcome and Histopathology in a Canine Model of Complete Cerebral Ischemia," *Anesthesiology*, vol. 83, No. 2, Aug. 1995, pp. 325–335.

William L. Lanier, "Cerebral Metabolic Rate and Hypothermia: Their Relationship with Ischemic Neurologic Injury," *Journal of Neurosurgical Anesthesiology*, vol. 7, No. 3, Jul. 1995, pp. 216–221.

Roy F. Cucchiara et al., "Clinical Neuroanesthesia," *Churchill, Livingstone*, pp. 207–209.

John C. Drummond and Harvey M. Shapiro, "Cerebral Physiology," *Anesthesia*, Third Edition, pp. 621–624.

Mark H. Zornow, M.D. et al., "Dexmedetomidine, an $\alpha_2$–Adrenergic Agoinst, Decreases Cerebral Blood Flow in the Isoflurane–Anesthetized Dog," *Anesth Analg*, vol. 70, 1990, pp. 624–630.

Robert F. Spetzler, M.D., et al., "Aneurysms of the basilar artery treated with circulatory arrest, hypothermia, and barbiturate cerebral protection,"*J. Neurosurg*; vol. 68, Jun. 1988, pp. 868–879.

Paolo Trubiano, M.D., et al., Jugular Venous Bulb Oxyhemoglobin Saturation During Cardiac Surgery: Accuracy and Reliability Using a Continuous Monitor, *Anesth. Analog.*, 1996, vol. 82, p. 964–968.

Olga Plattner, M.D. et al., Rapid Core–to–Peripheral Tissue Heat Transfer During Cutaneous Cooling, *Anesth Analg*, 1996, vol. 82, pp. 925–930.

L.M. Milde, "Cerebral protection, Clinical Neuroanesthesia," Churchill Livingstone, New York, 1987, pp. 207–209.

"Heart and Stroke Facts: 1996 Statistical Supplement," *American Heart Association*, Dallas, p. 20–22.

SELECTIVE CONVECTIVE BRAIN COOLING APPARATUS AND METHOD

This application claims filing priority from U.S. provisional application Ser. No. 60/042,931, filed Apr. 3, 1997.

TECHNICAL FIELD OF THE INVENTION

This invention generally relates to cooling a patient and, more particularly, to a method for selectively cooling the brain during any situation in which the brain may be at risk of injury, including, for example, normothermic or hypothermic cardiopulmonary bypass, head injury, stroke, cardiac arrest, or neurosurgical procedures.

BACKGROUND OF THE INVENTION

In recent years, improved surgical technique and myocardial preservation during procedures involving cardiopulmonary bypass (CPB) have significantly reduced perioperative cardiac, and overall, morbidity and mortality. However, despite major advances in myocardial protection during CPB, patients undergoing CPB and heart surgery continue to sustain significant rates of postoperative alterations in neurologic and neuropsychologic function. These changes range from subtle neurologic deficits (e.g., patients "do not seem to be themselves"), to overt sensorimotor deficits (e.g., stroke), to post-operative brain death. For example, investigators—using state of the art testing techniques—have identified neurologic deficits (i.e., fatal cerebral injury, stroke, impaired level of consciousness, and seizures) in 1–6% of patients following CPB. See Mills SA: Cerebral injury and cardiac operations. Ann Thorac Surg 1993; 56:S86–91, which article is incorporated herein by reference. They also noted neuropsychologic deficits (i.e., cognitive changes quantified with tests of memory, learning, and speed of visual-motor response) in 60–80% and 20–40% of patients at 1 wk and 8 wk following cardiac surgery, respectively. Other investigators have reported that neurologic injury is the second most frequent cause of death (i.e., accounting for approximately 20% of CPB-related deaths) following CPB. See Nussmeier NA, Arlund C, Slogoff S: Neuropsychiatric complications after cardiopulmonary bypass: Cerebral protection by a barbiturate. Anesthesiology 1986; 64:165–170, which article is incorporated herein by reference. Thus, there is a need for a method to simultaneously optimize both cardiac and neurologic outcome following CPB and, in particular, following cardiac surgery.

It is widely believed that neurologic injury accompanying CPB is of an ischemic origin. Specifically, it is believed that during CPB low flow states and showers of air and particulate emboli washed into the cerebral circulation produce an ischemic insult that is primarily of a multifocal ischemic pattern. There is ample experimental evidence—predominantly using transcranial Doppler (TCD)-facilitated assessment of the cerebral circulation—to support this theory. For example, Mills described mean embolic counts (i.e., the mean number of discrete embolic events detected) of 50 and 207 in coronary artery bypass grafting (CABG) patients having an aortic plaque thickness measuring <5 mm and >5 mm, respectively. Albin et al. (see Albin MS, Hantler GB, Mitzel H: Aeric microemboli and the transcranial Doppler (TCD): Episodic frequency and timing in 62 cases of open heart surgery. Anesthesiology 1991; 75:A53, which article is incorporated herein by reference.) reported a mean embolic count of approximately 360 at the completion of CPB in patients having "open" heart surgery (e.g., as occurs with valve repair or replacement). In contrast, patients having "closed" heart surgery (e.g., as occurs with CABG) experienced half that number of air emboli at the same study interval. These observations correlate well with a more than two-fold greater incidence of postoperative neuropsychiatric deficits in "open" versus "closed" heart surgery patients. See Slogoff S, Girgis KZ, Keats AS: Etiologic factors in neuropsychiatric complications associated with cardiopulmonary bypass. Anesth Analg 1982; 61:903–911, which article is incorporated herein by reference. Albin et al. also reported previously unsuspected episodes of no cerebral blood flow (CBF) ranging in duration from 4 s to longer than 2 min during otherwise apparently uneventful CPB. The latter events, while insufficient to cause irreversible brain injury alone, may be sufficient to exacerbate injury resulting from air and particulate emboli.

It is also well known that alterations in temperature can affect the brain's ability to survive an ischemic insult. This phenomenon has been demonstrated repeatedly in humans subjected to profound hypothermia and circulatory arrest to facilitate the surgical repair of complex cardiac or cerebrovascular anomalies. When temperature is reduced to 17–20° C., the human brain can tolerate approximately one hour of circulatory arrest without sustaining permanent injury. This dramatic evidence of cerebral protection is believed to be mechanistically related to large reductions in the cerebral metabolic rate of oxygen consumption ($CMRO_2$) that occur during profound hypothermia. It has also been demonstrated that mild alterations in brain temperature can have a significant effect on functional outcome and histopathology following cerebral ischemia. In these studies, improvement in outcome was reported with mild hypothermia and worsened with mild hyperthermia.

The most dramatic examples of modulation of ischemic brain injury by small alterations in brain temperature have been reported by Wass et al. (See Wass CT, Lanier WL, Hofer RE, Scheithauer BW, Andrews AF: Temperature changes of $\geq 1°$ C. alter functional neurologic outcome and histopathology in a canine model of complete cerebral ischemia. Anesthesiology 1995; 83:325–335, which article is incorporated herein by reference) and Warner et al. (See Warner DS, McFarlane C, Todd MM, Ludwig P, McAllister AM: Sevoflurane and halothane reduce focal ischemic brain damage in the rat: Possible influence in thermoregulation. Anesthesiology 1996; 79:985–992, which article is incorporated herein by reference). The former investigators discovered that temperature changes of either 1 or 2° C. altered functional and histologic outcome in a canine model of complete cerebral ischemia. The latter authors discovered that a change in brain temperature of 1.2° C. altered functional and histologic outcome in a rat model of focal cerebral ischemia.

Although the exact physiologic basis by which small temperature changes produce significant alterations in post-ischemic neurologic outcome is not clear, it is apparent such changes can have a significant effect on functional outcome and histopathology following cerebral ischemia.

One technique known in the prior art for attempting to achieve cerebral cooling during major vascular or complex cardiac surgery has been attempted by packing the patient's head in ice. However, this technique suffers from various drawbacks, including posing a serious risk of frostbite injury to the patient.

SUMMARY OF THE INVENTION

The present invention provides a method and apparatus for selectively cooling the brain to reduce the risk of brain injury from various medical conditions or clinical procedures, and allows for selective cooling of the brain—independent of core temperature—using non-invasive convective cerebral cooling.

The present invention may also include the step of selectively controlling cerebral blood flow (CBF) and/or cerebral metabolic rate (CMR) in conjunction with convective cooling of the brain to further reduce the incidence of brain injury in various medical conditions or clinical procedures.

The present invention also allows for maintenance of the brain in a hypothermic state relative to core temperature during the rewarming phase of hypothermic cardiopulmonary bypass thereby preventing hyperthermia in the brain during the rewarming phase of hypothermic CPB.

The present invention also advantageously provides for selective cooling of the brain while minimizing the risk of frostbite or other thermal injury to the patient being cooled.

A significant benefit of the present invention is that by allowing for selective cerebral cooling, cardiac surgical teams may be able to more frequently employ normothermic CPB in patients undergoing CABG or repair of intracardiac anomalies, without concern for exacerbating the risk of ischemic neurologic injury. Specifically, the net result of selective cerebral cooling in patients undergoing normothermic CPB should be an improvement in cardiac (associated with normothermic CPB) and neurologic (due to selective brain cooling) outcomes following surgery while avoiding adverse changes in systemic physiology such as, cardiac arrhythmias, myocardial ischemia, decreased myocardial contractility, and coagulopathy.

In one preferred embodiment, the present invention provides for the application of forced, cool air to the intact cranial surface, resulting in convective brain cooling to values below core temperature in humans during CPB, head injury, stroke, cardiac arrest, or neurosurgical procedures. It will be apparent that the temperature of the cooled air may be modified within a suitable range to achieve the desired degree of brain cooling.

In another embodiment the present invention may include the step of selectively controlling CBF and/or CMR in conjunction with convective cerebral cooling.

In still another embodiment the present invention may include the step of administering an anesthetic in conjunction with convective cerebral cooling.

The present invention may also include the step of providing cooled air to both the patient's head and neck region and dispersing the cooled air over this entire region resulting in convective cooling of the brain.

DESCRIPTION OF THE PREFERRED EMBODIMENTS

As discussed previously, changes in patient management during surgery and, particularly, cardiac or major vascular surgery, have resulted in a significant: a) improvement in postoperative cardiac function and outcome, and b) decrease in overall perioperative mortality.

Traditionally, CPB has been performed using systemic hypothermia (i.e., maintaining the core temperature at $\leq 28°$ C.) as a means of providing organ (e.g., brain) protection during cardiac or major vascular surgery. However, a current trend in cardiac surgery is "warm" or normothermic (i.e., maintaining the core temperature at, or near, 37° C.) CPB. The rationale for this dramatic shift in systemic temperature management strategy stems from recent investigations reporting significant improvements in postoperative cardiac function and outcome when compared to patients undergoing hypothermic CPB. However, when using the normothermic systemic temperature management, the brain is not cooled, does not benefit from hypothermia, and thus, remains at high-risk for ischemia-related injury. Accordingly, the use such temperature management protocols has resulted in a significant worsening of neurologic outcome [e.g., patients experience up to a three-fold increase in the incidence of adverse neurologic events (including stroke)] following normothermic CPB. Taken together, although normothermic CPB improves cardiac outcome, it has not gained widespread clinical acceptance in the United States due to its potentially detrimental effect on the brain.

The potential magnitude of CPB-related brain injury is not trivial and the downstream effect of brain injury following CPB is devastating—socially and fiscally—to patients, family members, and society. Neurologic injury is probably the most common source of morbidity, and the second most frequent cause of death (i.e., accounting for approximately 20% of CPB-related deaths) following cardiac surgery. In the United States, it is estimated that 485,000 CABG operations will be performed in 1996. Of these, major neurologic deficits (e.g., fatal cerebral injury, stroke, impaired level of consciousness, and seizures) will occur in up to 6% of patients following CPB (i.e., up to 29,100 major events in 1996). In addition to major neurologic events, neuropsychologic deficits (i.e., cognitive changes quantified with tests of memory, learning, and speed of visual-motor response) occur in 60–80% and 20–40% of patients at 1 wk and 8 wk following cardiac surgery, respectively.

The method and apparatus of the present invention selectively cools the brain independent of the body's core and, thereby, allows for the benefits of normothermic CPB while providing for the benefits of selective brain cooling.

The description will now turn to the apparatus and method of a presently preferred embodiment of the invention. A coverlet shown generally in FIGS. 5a and 5b and denoted by reference numerals 10 and 10'—also referred to throughout this disclosure as a helmet or blanket—is designed to provide the benefits of brain hypothermia during CPB, head injury, stroke, cardiac arrest, or neurosurgical procedures. In a preferred embodiment, the coverlet 10 provides convective cooling of the brain by passing cooled air about the head and neck region of the patient in a substantially enclosed environment to minimize cooled air losses.

Figure 5A:
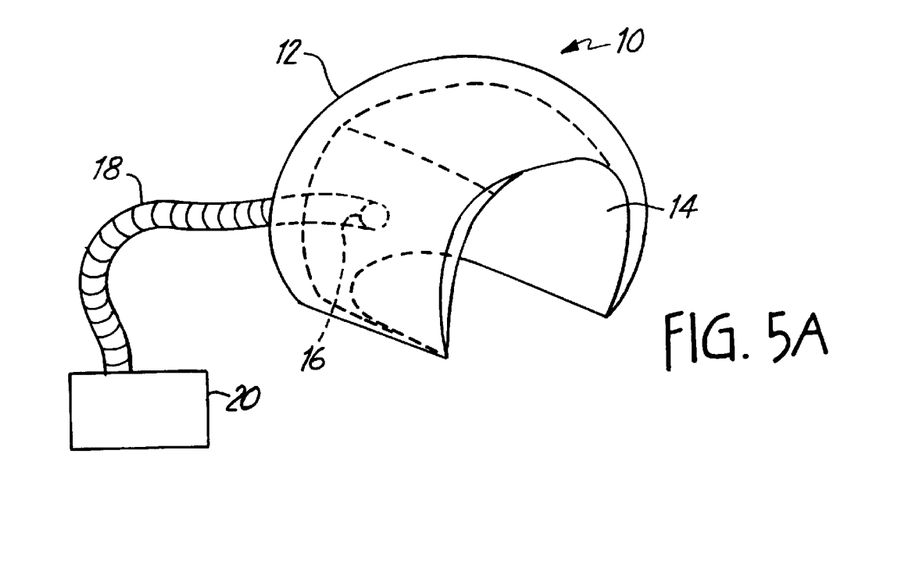
FIG. 5a depicts one embodiment of a coverlet of the resent invention.

The coverlet is preferably constructed of soft, flexible materials to surround the area of the head and neck region in which cooling is desired. As shown in FIG. 5a, the hood-like coverlet 10 has two layers, an outer insulating layer 12 and an inner air diffusing layer 14. The coverlet is interfaced with an air cooling device 20 through an inlet port 16 and an air hose 18. This air cooling device 20 provides forced, cooled air to the coverlet 10. This air passes between the two layers 12, 14 and disperses throughout the coverlet 10. This dispersed cooled air then diffuses through the air diffusing layer 12 toward the patient's head and neck region, thereby convectively cooling the head and neck, and ultimately the brain.

The air cooling device 20 is preferably the PolarAir™ unit manufactured by Augustine Medical. This unit provides 1000 1/min air at 10° C., which results in a temperature of about 13° C. at the coverlet. However, even more preferable would be a device that is capable of only providing cooled air which capability the Augustine device does not have. Further, it is to be understood that the choice of air cooling device is not a critical feature of the present invention and any such device which is capable of providing sufficient amounts of cooled air to the helmet may be employed.

The outer, insulating layer 12 of the coverlet is preferably a plastic or other suitable material that provides insulation, is formable to the desired configuration of the coverlet, and is medically compatible with the surgical environment. Such suitable materials are known to those of skill in the art. This outer layer prevents the cooled air from escaping into the surrounding environment, thus ensuring rapid and efficient air diffusion through the inner layer 14, which results in convective cooling of the patient's brain.

The inner, air diffusing layer 14 of the coverlet may be any of a number of suitable porous materials known in the art. The material must be formable to the desired configuration of the coverlet, as well as being compatible with the medical environment. In addition, the material must diffuse the cooled air rapidly, and at a large enough flow rate to provide rapid and reliable brain cooling. In a preferred embodiment, the air diffusing material is perforated to increase cooled air flow around the patient's head and neck region, and improve the convective cooling of the brain.

The coverlet is preferably designed to surround the head and neck region of a patient, but may also be designed only for the head region. The coverlet need not be in contact with the patient's skin or scalp, but may form an air space of, for example, about one to three inches from the patient's skin or scalp to allow for convective cooling. Numerous embodiments of this coverlet are possible to meet the needs of the patient and the surgical environment. These embodiments include various options that can be available alone, or in combination with other options. These options are described herein.

When creating a hypothermic environment in contact with a patient's skin and scalp, it is necessary to ensure that excessive cooling does not occur in vulnerable locations, such as ears, nose and lips, thereby creating potential for frostbite. Frostbite is defined as localized cold-induced tissue injury. Historically, frostbite has been divided into a series of four pathologic (prefreeze, freeze-thaw, vascular stasis, and late ischemic) phases. The least injurious of these (i.e., the prefreeze phase) occurs when the tissue temperature decreases to <10° C. Remaining phases emerge with progressive cooling and ice crystal formation. The extent of tissue injury depends on the: a) magnitude of hypothermia, b) duration of exposure, c) presence or absence of wind chill, d) relative humidity, and e) surface moisture content.

In the setting in which the present invention is to be utilized—normothermic CPB and selective cerebral cooling—, the incidence of cold-induced tissue injury is unlikely for the following reasons: (1) First, the cooling device utilized in various embodiments blows approximately 1000 1/min air at 10° C. However, the actual temperature of the cool air leaving the distal end of the unit is about 13° C. (i.e., 3° C. warmer than the 10° threshold previously reported to initiate cold-induced tissue injury); (2) Second, at tissue temperatures of approximately 15° C., integumentary vasculature undergoes periodic vasodilation. These episodes of vasodilation are thought to serve a thermoprotective role. Again, the actual temperature at the skin surface will likely exceed (by ≧about 5° C.) the 10° C. threshold previously reported to initiate cold-induced tissue injury; (3) Third, the cooling device utilized in various embodiments of the present invention (PolarAir™ unit manufactured by Augustine Medical) has withstood the rigorous scrutiny of the Food and Drug Administration (FDA) and has received approval for human use (FDA approval number: K 950416); and (4) Fourth, using the same convective device, previous studies have reported no complications—including frostbite—in humans exposed to hours of systemic cooling.

Taken together, it is believed that the likelihood of iatrogenic cold-induced injury is remote or nonexistent. However, as a precautionary measure, to guard against frostbite, in a preferred embodiment the coverlet is provided with transparent window areas positioned to allow observation of critical body areas. In another related embodiment, the transparent windows may be opened by sliding to allow access to, as well as observation of, the body areas. In another embodiment the transparent windows may be removable to allow access. In another embodiment the coverlet is provided with a craniotomy opening to allow access to the patient's head. This access makes brain surgery and other surgical head procedures possible while still providing a selectively hypothermic environment for the brain.

In some situations, it is desirable to specifically cool the patient's neck, whereas in other situations this is not necessary or not desired. Therefore, in a preferred embodiment, the coverlet is provided with a neck collar that allows for the cooling of the neck specifically, in the same convective manner, as described herein. In another embodiment, the coverlet does not extend to the neck region and covers only the head. In yet another embodiment, a cooling head cushion with circulating chilled water or air may be placed under the patient's head to further cool the brain. In yet another embodiment, an oral pharyngeal cooling device such as a cooled water bath or air current may be utilized to provide further cooling. It is also within the scope of the present invention to include in conjunction with the convective cooling method additional cooling through the use of any of a variety of cool water misting devices which are well known in the art and/or the use of a network of capillaries placed around the head and/or the neck circulating a chilled liquid such as water to provide additional conductive cooling. In a preferred embodiment, the capillaries are elastic and sized such that they may fit snugly around the head.

As stated above, the incoming cooled air passes between the outer and inner layers of the coverlet to be dispersed and ultimately diffused about the patient's head and neck region. The result is an air mattress-like effect. In the surgical environment, there are many sharp instruments in use which are capable of puncturing the coverlet 10, causing failure of the brain cooling invention. Therefore, in a preferred embodiment, the outer layer 12 is constructed to form discrete air chambers 28 when under pressure such that failure of one chamber 28 does not result in failure of the entire cooling device.

The coverlet, as described above, may be constructed from materials that result in a reusable unit that is capable of being suitably prepared for subsequent patients. However, in another embodiment the coverlet may be constructed from materials that result in a disposable unit.

Figure 5B:
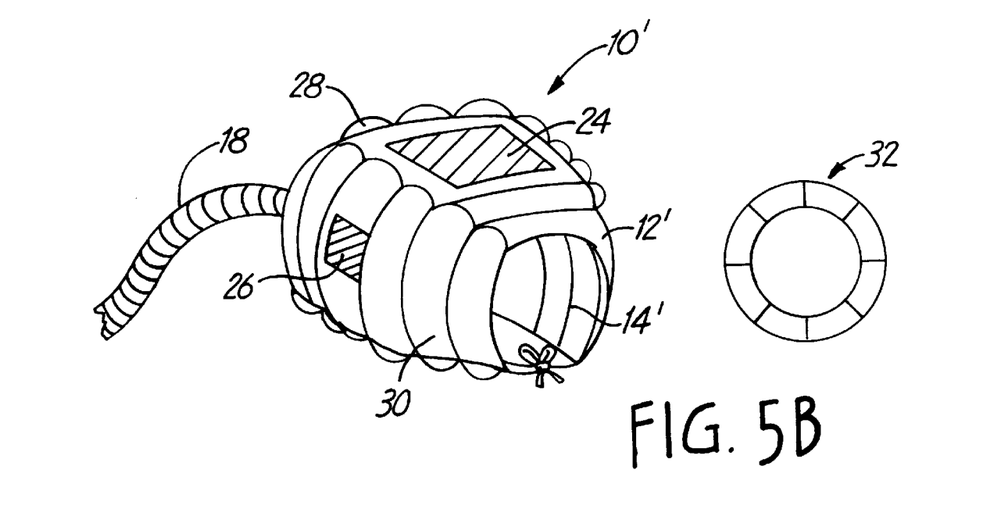
FIG. 5b depicts an alternative embodiment of a coverlet of the present invention.

To aid in a more homogeneous cooling of the patient's entire head and neck region, another embodiment of the convective cooling device may include a cooling head cushion 32 as shown in FIG. 5b. The cooling head cushion 32 may be cooled by the circulation of either chilled water or cool air. The patient's head would rest on this cushion while on the operating table. The cooling cushion 32 would be suitable for the surgical environment, and would provide either conductive or convective cooling of the patient's dependent brain regions. The term dependent is used here to refer to that portion of the patient's head which is contacting the cooling cushion 32.

In FIG. 5b, a coverlet 10' is shown in which a number of the above described preferred embodiment options are incorporated. The hood-like coverlet 10' also has two layers, an outer insulating layer 12' and an inner air diffusing layer 14', and is fed cooled air via hose 18. In this embodiment, the outer layer 12' is constructed with numerous discrete air chambers 28 to aid in maintaining air cooling after a puncture, or similar event. In addition, the coverlet 10' is provided with transparent windows 24 and 26 which allow for observation of the patient's face and ears during surgery, in order to minimize the possibility of frostbite during the procedure. The coverlet 10' is also provided with a neck collar 30 that secure about the patient's neck, which aids in additional convective cooling of the head and neck region.

Figure 1:
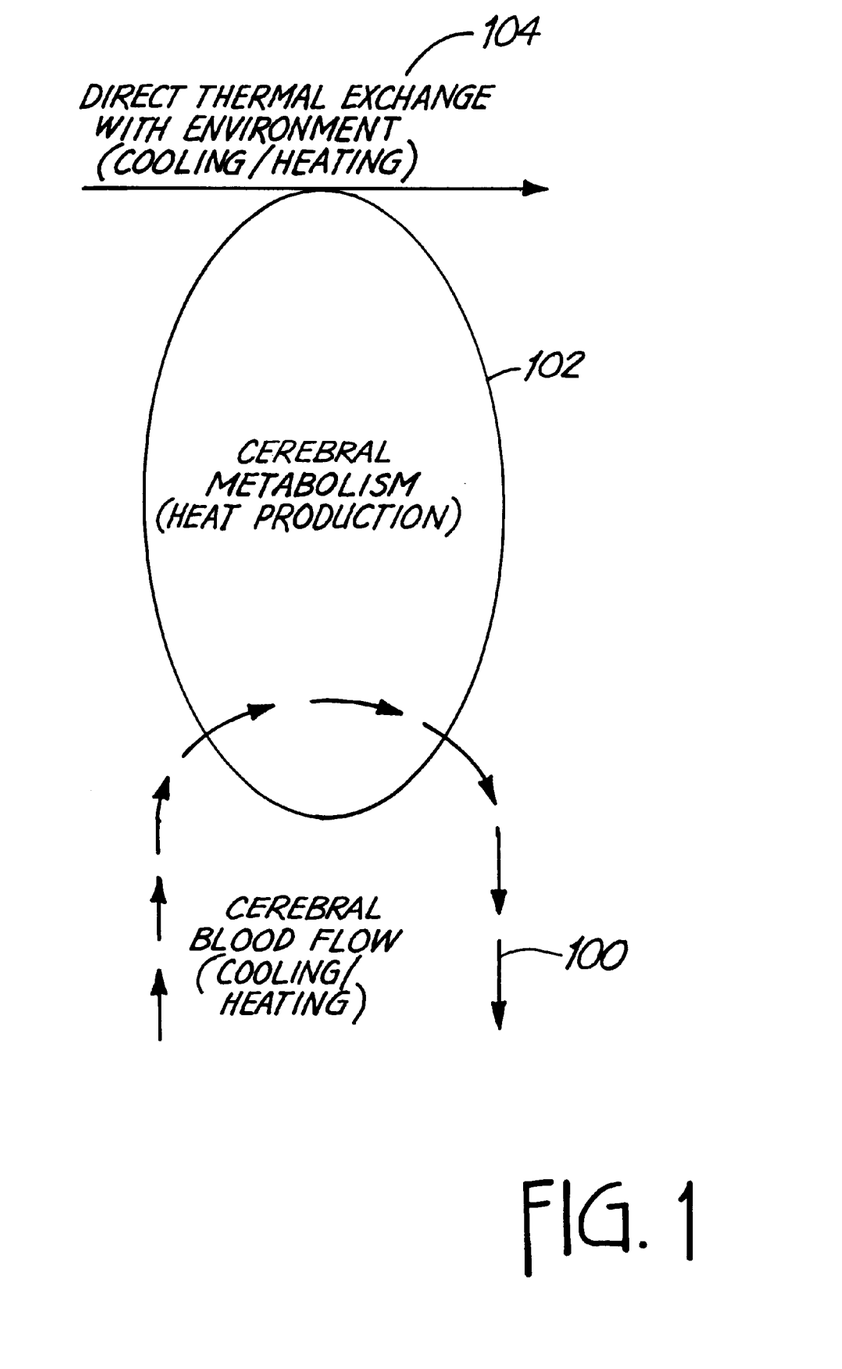
FIG. 1 is a high-level depiction of the primary factors which are determinants on brain temperature.

As depicted in FIG. 1, the primary determinants of brain temperature are heat exchange with the body's core modulated by cerebral blood flow temperature, shown generally by reference numeral 100 ("cerebral blood flow"); heat production resulting from cerebral metabolism, shown generally by reference numeral 102 ("cerebral metabolism"); and direct thermal exchange with the environment, shown generally by reference numeral 104 ("extracerebral environment").

Each factor is discussed separately: *Cerebral blood flow*, 100: Depending on the baseline core-to-brain temperature gradient, cerebral circulation can potentially warm or cool the brain. For example, if the brain is cooler than core temperature, cerebral circulation results in a net increase in brain temperature. In contrast, if the brain is warmer than core temperature, cerebral circulation results in a net cooling of the brain. This explains why there is typically good agreement between core and brain temperatures in the brain of awake patients, or in the brain of those anesthetized with an anesthetic that minimally affects basal CBF and CMR. In contrast, when CBF is interrupted (i.e., cerebral ischemia is induced) in the previously normal brain, the brain tends to lose heat to the environment, and the brain becomes cooler than core.

*Cerebral metabolism*, 102: The brain has one of the highest metabolic rates in the entire body. This metabolism produces heat and results in brain temperatures, at rest, that are slightly warmer than core temperature. Anesthetics alter the CMR and thus have the potential to alter cerebral heat production and the relationship between brain and core temperatures.

*Extracerebral environment*, 104: The third determinant of brain temperature is heat exchange with the environment. This thermal environment is generally defined in terms of the surrounding muscle and bone, as well as the extracorporel environment. In the normal, intact head, the brain's immediate environmental temperature (i.e., of bone, muscle, and skin) will approximate—or be slightly less than—core temperature. However, if the immediate environmental temperature is lowered further, the temperature of the brain should decrease, beginning with the outermost brain layers.

It should be appreciated that the present invention, in the various embodiments previously set forth, may influence each of the three primary determinants of brain temperature 100, 102 and 104.

In conjunction with convective cerebral cooling, CBF 100 and/or CMR 102 may be selectively controlled to maintain, or increase, the magnitude of the temperature gradient between the patient's brain and body core. As an example, various agents such as anesthetics may be selectively utilized to have a desirable effect on brain-to-core temperature gradients. This is because anesthetics may dramatically alter baseline CBF 100 and CMR 102, and thereby alter the relationship between core and brain temperatures. Thus, the method of the present invention may include the step of administering a selected anesthetic. In a preferred embodiment, a vasoconstrictor such as a high-dose barbiturate, etomidate, propofol, or any means of inducing cerebral vasoconstriction—which produces reductions in CMR—may be administered. Such drugs are cerebral vasoconstrictors and are believed to be responsible for the creation of a physiologic barrier between the core and brain temperatures, resulting in a net cooling of the brain.

Alternatively, CBF 100 may be altered using $CO_2$-mediated vasoconstriction or vasodilation techniques which are known in the art.

As previously mentioned, studies on dogs (the results of which are discussed below) have shown that temperature changes of as little as 1 or 2° C. altered functional and histologic outcome. During a recent study, (see Wass CT, Cable DG, Schaff HV, Lanier WL: Anesthetic Technique Influences Brain Temperature During Cardiopulmonary Bypass In Dogs. Ann Thorac Surg 1998; 65:454–60, which article is incorporated herein by reference), the novel hypothesis that brain protection by barbiturates is mediated in part by drug-induced gradients between brain and core temperatures was tested. This hypothesis was tested in a canine model in which core temperature was manipulated using CPB while allowing brain temperature to follow passively. As discussed below, these studies support the efficacy of the method and apparatus of the present invention. The studies reveal that selectively cooling the brain during situations where the brain may be at risk of injury, including, normothermic or hypothermic cardiopulmonary bypass, head injury, stroke, incidences of cardiac arrest and neurosurgical procedures, reduces the risk of neurologic injury.

EXAMPLES

Results of Study Entitled "Anesthetic Technique Influences Brain Temperature During Cardiopulmonary Bypass in Dogs"

Purpose-bred dogs were anesthetized with either: (a) i.v. pentobarbital in a dose sufficient to produce an isoelectric electroencephalograph, or (b) inhaled halothane 1.0 MAC. Dogs were maintained at normocapnia throughout the study, and blood pressure was maintained near 90 mmHg using a phenylephrine infusion. Temperatures were monitored by placing thermistors bilaterally beneath the temporalis muscle, in the parietal epidural space, and in the parietal brain parenchyma at depths of 1 cm and 2 cm beneath the dura. When examined at the time of brain dissection, the distal tip of the 1 cm and 2 cm intraparenchymal needle thermistors were observed in subcortical and basal ganglia structures, respectively. Core temperature was measured from a thermistor placed in the esophagus, at the level of the right atrium (confirmed by palpation at the time of thoracotomy). Prior to instituting CPB, all temperatures were controlled at 38.0±0.2° C. (mean±range). Thereafter, atrio-femoral CPB was initiated, and after a 15 min period of CPB at 38° C.—core temperature was decreased to 28° C. over approximately 21 min. Following 30 min at 28° C., the core temperature was returned to 38° C. over approximately 21 min, and maintained at 38° C. for the next 30 min. The resulting brain temperatures were recorded, and brain-to-core temperature gradients were calculated by subtracting the core temperature from the brain temperature. Data between groups were compared using unpaired t-tests. $P<0.05$ was considered significant.

Figure 2:
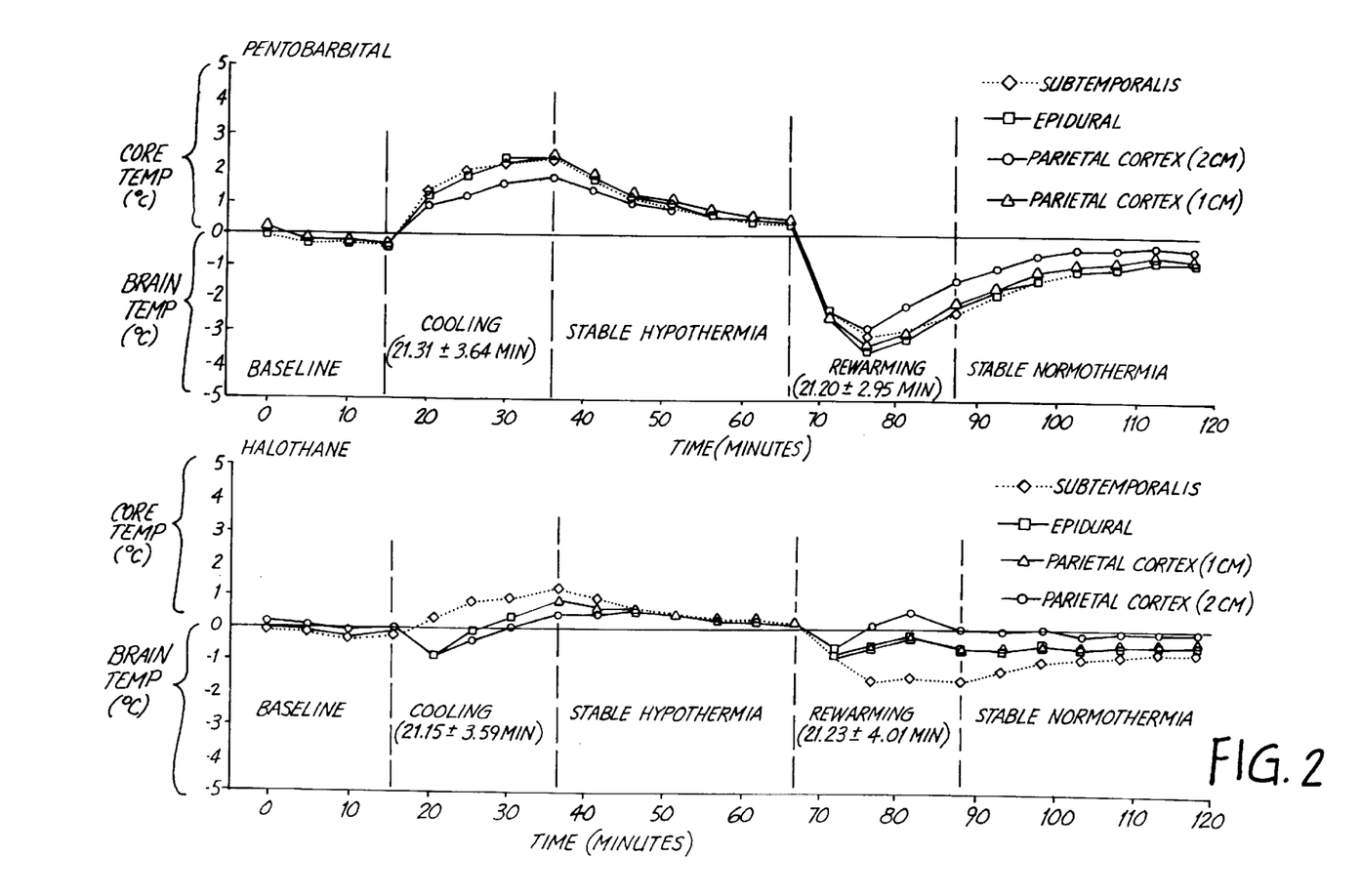
FIG. 2 illustrates thermal gradients in pentobarbital- or halothane-anesthetized dogs undergoing hypothermic cardiopulmonary bypass.

As shown in FIG. 2, it was demonstrated that in halothane-anesthetized dogs, mean brain-to-core temperature gradients were always $>1.0°$ C., for all brain sites, during all phases of CPB. In contrast, during active cooling—though pentobarbital-anesthetized dogs experienced concomitant decreases in brain and core temperatures—mean brain temperatures typically exceeded the core by 1.7 to 2.2° C. This brain-to-core temperature gradient persisted into the period of stable hypothermia. During the rewarming phase of CPB, the mean brain temperature was 2.9 to 3.4° C. cooler than the core. This trend of relative cerebral hypothermia persisted well into the period of which the core temperature was 38° C. Differences between the two anesthetic groups were statistically significant.

FIG. 2 is summarized as follows: Thermal gradients in pentobarbital- or halothane-anesthetized dogs undergoing hypothermic cardiopulmonary bypass are shown. The gradient between pericranial and brain temperatures versus core (esophageal thermistor placed to the level of the right atrium) temperature, as assessed by thermistors placed: (a) beneath the temporalis muscle, (b) in the epidural space, (c) 1 cm deep in the cortex, and (d) 2 cm deep in the cortex. Gradient was calculated as reference temperature minus core temperature. Hence, a positive value denotes that the measurement site was warmer than the core; a negative value denotes that the measurement site was cooler than the core.

Based on the results depicted in FIG. 2, it was concluded that deep barbiturate anesthesia resulted in an uncoupling of brain and core temperatures that was not present during halothane anesthesia. The differences were attributed primarily to the differing effects of the two anesthetics on CBF and CMR. That is, deep barbiturate (i.e., a cerebral vasoconstrictor) but not halothane (i.e., a cerebral vasodilator) anesthesia created a physiologic thermal barrier between acute changes in core temperature and brain temperature. Thus, the gradients observed may be of relevance to the mechanisms by which anesthetics protect the brain from ischemic injury.

It is believed that—by interfering with heat exchange between the body's core and brain—pentobarbital should enhance the influence of environmental temperature on brain temperature. Consideration of this factor for use with the present invention allows one embodiment of the present invention (that including the step of administering a selected anesthetic) to influence the ability to decrease brain temperature using surface cooling techniques.

Using similar experimental conditions as cited above, a study was completed in which a non-invasive technique allowing for selective cooling of the brain independent of core temperature. That is, in the setting of either hypothermic or normothermic CPB, there was initiated and maintained the pericranial (i.e., the environment immediately surrounding the intact calvarium) temperature near 13° C. using a convective cooling device manufactured by Augustine Medical, Eden Prairie, Minn. The device, the Polar Air,® delivered approximately 1000 1/min air at 10° C.; however, the temperature measured (using a flexible thermistor) and recorded at the cerebral coverlet, shown generally by the reference numeral 10 in FIG. 5a, was about 13° C.

The following are the results of studies performed on dogs to determine if it was possible to induce clinically important gradients (i.e., gradients having a magnitude of ± the 1° C. previously reported to modulate outcome following cerebral ischemia) between brain and core temperatures using selective convective cerebral cooling.

Efficacy of Selective Cerebral Cooling During Hypothermic CPB

Figure 3:
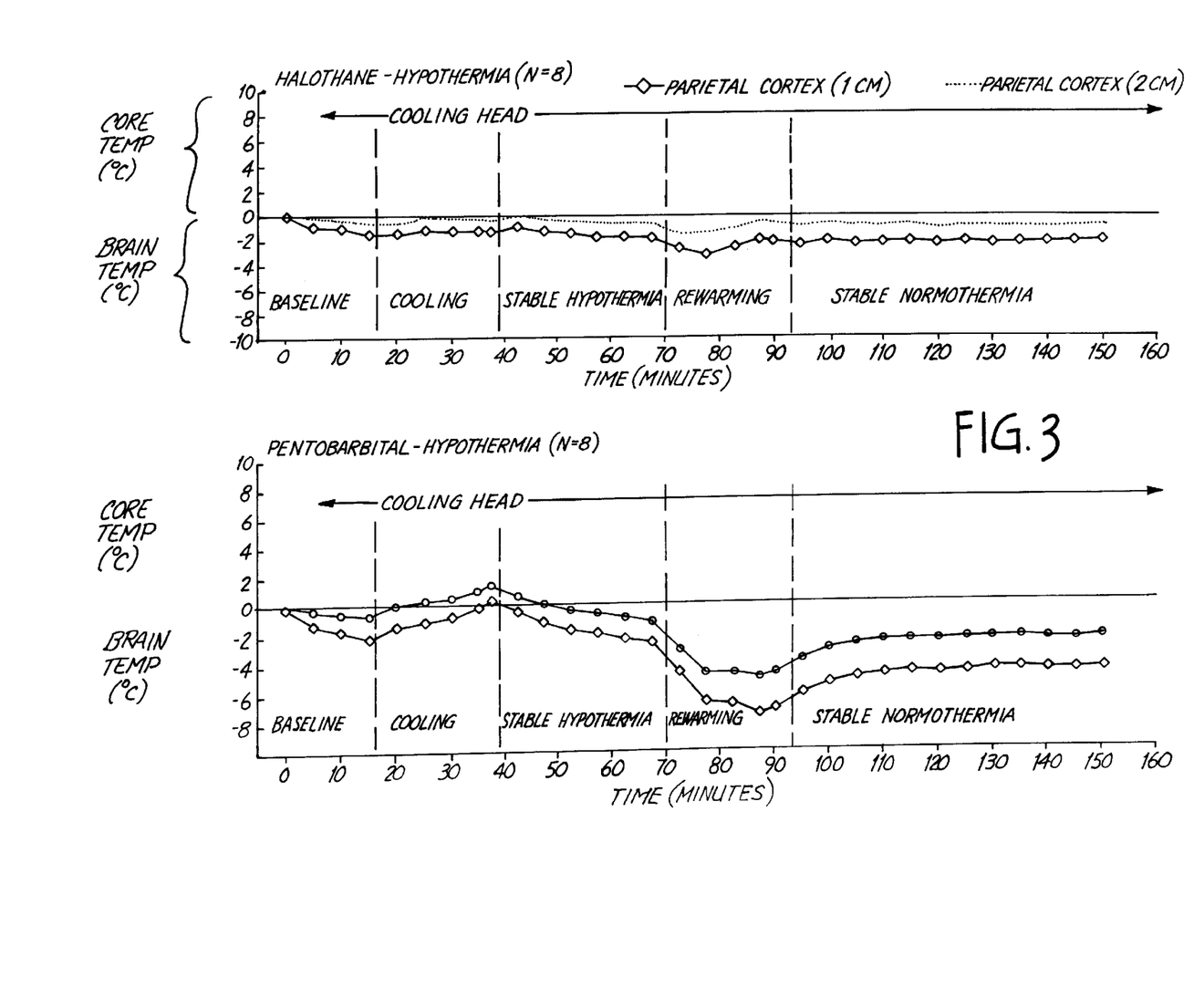
FIG. 3 illustrates thermal gradients in pentobarbital- or halothane-anesthetized dogs undergoing hypothermic cardiopulmonary bypass with simultaneous convective cerebral cooling.

In halothane-anesthetized dogs (n=7), it was demonstrated that mean brain temperatures, at 1 cm beneath the dura, were 1.2 to 2.1° C. cooler than the core during all phases ($p<0.05$ for each phase), except baseline, of CPB (Table 1, FIG. 3). At 2 cm beneath the dura, the mean brain-to-core temperature gradients were always $\leq 1°$ C. during all phases of CPB (Table 1, FIG. 3). In contrast to the precedent data, acquired in halothane-anesthetized dogs undergoing hypothermic CPB without selective cerebral cooling (i.e., had their cranium exposed to ambient room temperature) (FIG. 2), selective cerebral cooling resulted in significant cerebral cooling, at 1 cm beneath the dura, during most phases of CPB.

FIG. 3 depicts thermal gradients in pentobarbital- or halothane-anesthetized dogs undergoing hypothermic CPB with simultaneous convective cerebral cooling in accordance with the present invention. The gradient between brain temperatures versus core (esophageal thermistor placed to the level of the right atrium) temperature, as assessed by thermistors placed: a) 1 cm deep in the cortex, and b) 2 cm deep in the cortex, were calculated as regional brain temperature minus core temperature. Hence, a positive value denotes that the regional brain temperature was warmer than the core; a negative value denotes that the regional brain temperature was cooler than the core.

Table 1. Brain-to-core Temperature Gradients in Halothane- or Pentobarbital-anesthetized Dogs Undergoing Hypothermic Cardiopulmonary Bypass

|  | Halothane Mean (Range) (° C.) | | Pentobarbital Mean (Range) (° C.) | |
| --- | --- | --- | --- | --- |
| Phase of CPB | 1 cm | 2 cm | 1 cm | 2 cm |
| Baseline | −0.7(−1.3 to 0.1) | −0.2(0.4 to 0.2) | −1.2(−1.8 to −0.1) | −0.3(−0.6 to 0.2) |
| Cooling | −1.2(−1.3 to −1.0) | −0.2(−0.3 to −0.1) | −0.8(−1.3 to −0.3) | 0.2(−0.2 to 0.8) |
| Stable hypothermia | −1.4(−1.8 to −0.7) | −0.5(−0.8 to −0.1) | −1.3(−2.3 to 0.2) | −0.1(−0.9 to 1.2) |
| Rewarming | −2.1(−2.8 to −1.6) | −1.0(−1.6 to −0.3) | −6.0(−6.8 to −4.5) | −4.0(−4.5 to −3.0) |
| Stable normothermia | −2.1(−2.4 to −1.6) | −1.0(−1.2 to −0.5) | −4.2(−6.4 to −3.0) | −2.2(−4.0 to −1.4) |

Brain temperatures were derived by averaging right and left values, measured at 1 or 2 cm beneath the dura, during each time interval (i.e., phase) of CPB. Brain-to-core temperature gradients were calculated by subtracting the core temperature from the brain temperature. Thus, a positive value denotes that the brain was warmer than the core; a negative value denotes that the brain was cooler than the core. p<0.05 represents statistical significance (using one-sample t-tests) when compared to core temperature. CPB=cardiopulmonary bypass.

In pentobarbital-anesthetized dogs (n=6), it was demonstrated that mean brain temperatures, at 1 cm beneath the dura, were 1.2 to 6.0° C. cooler than the core during all phases, except systemic cooling, of CPB (Table 1, FIG. 3). Specifically, the mean brain temperatures were 6.0 (range: 4.5 to 6.8° C.) (p<0.001) and 4.2° C. (range: 3.0 to 6.4° C.) (p<0.001) cooler than the core during the rewarming and stable normothermia phases of CPB, respectively. Similar trends were noted at a brain parenchymal depth of 2 cm; however, the magnitude of cooling was less profound. Specifically, mean brain temperatures were approximately 4.0 (range: 3.0 to 4.5° C.)(p<0.001) and 2.2° C. (range: 1.4 to 4.0° C.) (p<0.001) cooler than the core during systemic rewarming and stable normothermia, respectively (Table 1, FIG. 3). When compared to precedent data, acquired in pentobarbital-anesthetized dogs undergoing hypothermic CPB without selective cerebral cooling (FIG. 2), selective cerebral cooling abolished episodes of relative cerebral hyperthermia noted during systemic cooling and stable hypothermia, and doubled the magnitude of brain cooling during systemic rewarming and stable normothermia.

During systemic rewarming and stable normothermia, differences between halothane-and pentobarbital-anesthetized groups were statistically significant, at both 1 and 2 cm beneath the dura (p≦0.008 and ≦0.003, respectively).

Although 3 dogs remained to be studied (i.e., to achieve n=8 in each group), it was concluded that selective cerebral cooling, during hypothermic CPB, typically resulted in brain temperatures that were significantly cooler than the 1° C. changes previously reported to modulate ischemic injury. These changes were particularly prominent in pentobarbital-anesthetized (i.e., an anesthetic possessing cerebral vasoconstricting properties) dogs during systemic rewarming and stable normothermia (i.e., periods in which the brain is at high-risk for ischemic injury). The magnitude of brain cooling was significantly greater than that observed in previous studies (FIG. 2) in which it was demonstrated that high-dose pentobarbital created a physiologic thermal barrier between acute changes in core and brain temperatures. Additionally, it was noted that the brain cooled at approximately the same rate as the core, and small brain-to-core temperature gradients were observed. Although small gradients were noted during systemic cooling and stable hypothermia, the brain was hypothermic, and thus, would be expected to benefit from cold-induced cerebral protective therapy. Taken together, when extrapolated to neurologic outcome following CPB in humans, selective convective cerebral cooling was shown to provide significant brain protection during phases of hypothermic CPB (i.e., during the rewarming and stable normothermia phases of CPB) in which the brain is often exposed to concomitant ischemia and relative hyperthermia.

Efficacy of convective cerebral cooling during normothermic CPB

The efficacy of selective brain cooling during normothermic cardiopulmonary bypass was also evaluated in dogs.

Using the same helmet design and study methods (except normothermic systemic temperature management) described in the above-mentioned studies, the novel hypothesis that selective convective cerebral cooling could decrease the brain temperature—independent of core temperature—during normothermic (i.e., had their core temperature maintained at 38° C. throughout the 150 min study period) CPB (FIG. 5) in dogs was tested. Again, dogs were randomly assigned to receive either halothane (n=7) or pentobarbital (n=7) anesthesia.

Figure 4:
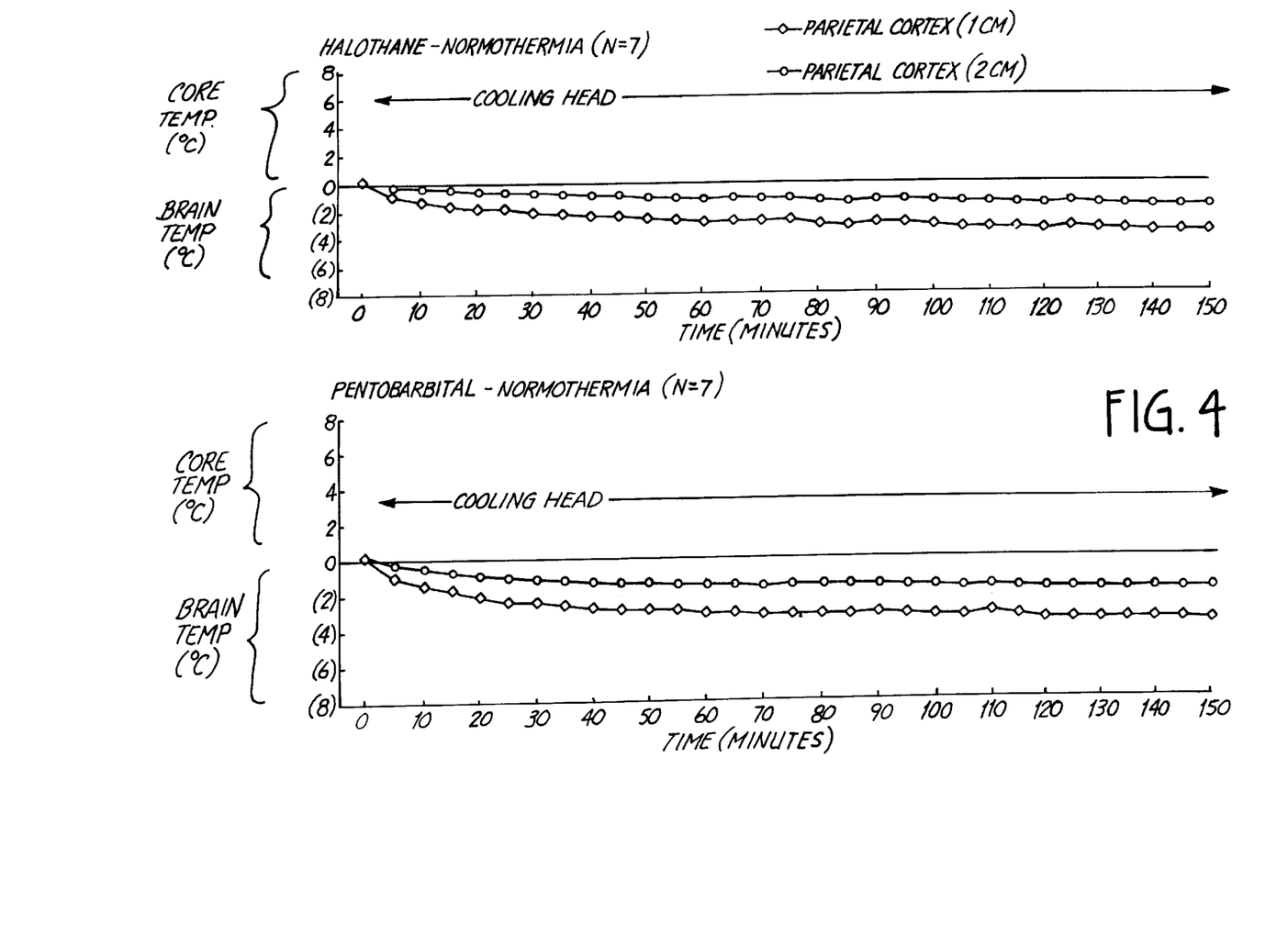
FIG. 4 illustrates thermal gradients in pentobarbital- or halothane-anesthetized dogs undergoing normothermic cardiopulmonary bypass with simultaneous convective cerebral cooling.

FIG. 4 depicts thermal gradients in pentobarbital- or halothane-anesthetized dogs undergoing normothermic cardiopulmonary bypass with simultaneous convective cerebral cooling. The gradient between brain temperatures versus core (esophageal thermistor placed to the level of the right atrium) temperature, as assessed by thermistors placed: a) 1 cm deep in the cortex, and b) 2 cm deep in the cortex, were calculated as regional brain temperature minus core temperature. Hence, a negative value denotes that the regional brain temperature was cooler than the core.

In halothane-anesthetized dogs, brain temperatures 1 cm (i.e., subcortical) and 2 cm (i.e., basal ganglia) beneath the dura were 2.1±0.90° C. (mean±SD) and 0.7±0.4° C. cooler than the core, respectively, after 30 min of CPB and cerebral cooling (FIG. 4). At the conclusion of the study (i.e., 150 min of CPB and cerebral cooling), these temperatures were noted to be 3.5±2.5° C. and 1.6±1.8° C. cooler than the core, respectively (FIG. 4).

In pentobarbital-anesthetized dogs, brain temperatures 1 cm and 2 cm beneath the dura were 2.6±1.4° C. and 1.2±0.6° C. cooler than the core, respectively, after 30 min of CPB and cerebral cooling (FIG. 4). There were no significant differences between groups.

Although 2 dogs remained to be studied (i.e., to achieve n=8 in each group), it was concluded that the magnitude of the temperature gradients was larger than the 1° C. changes previously reported to modulate ischemic injury. Additionally, the efficiency of the cooling device was sufficient to overwhelm any pharmacologically-induced physiologic thermal barrier noted in previous studies from our laboratory (see above). Taken together, when extrapolated to humans undergoing normothermic CPB, it is envisioned that selective convective brain cooling may enable clinicians to simultaneously improve both cardiac (i.e., resulting from normothermic CPB) and neurologic (i.e., resulting from hypothermia-mediated brain protection associated with selective cerebral cooling) outcomes following cardiac surgery.

The embodiments described above are intended to be representative and not limiting. Additional embodiments of the invention are within the claims.

What is claimed is:

1. A method for lowering brain temperature independent of core temperature in a patient, comprising the steps of:
   selectively providing a flow of cooled air to the patient's head, and
   dispersing the cooled air to convectively cool the head, sufficiently to maintain the brain in a hypothermic state temperature.

2. The method of claim 1, in which the cooled air is at a temperature of about 13° C. when being provided to the patient's head and neck region.

3. The method of claim 1, further comprising the step of selectively controlling cerebral blood flow to maintain or increase the magnitude of the temperature gradient between the brain and the patient's body core.

4. The method of claim 3, wherein the step of selectively controlling cerebral blood flow comprises administering an agent which controls cerebral blood flow.

5. The method of claim 4, wherein the agent comprises a cerebral vasoconstrictor.

6. The method of claim 4, wherein the agent comprises a cerebral vasodilator.

7. The method of claim 3, wherein the step of selectively controlling cerebral blood flow comprises the technique of $CO_2$-mediated vasoconstriction.

8. The method of claim 3, wherein the step of selectively controlling cerebral blood flow comprises the technique of $CO_2$-mediated vasodilation.

9. The method of claim 1, further comprising the step of selectively controlling cerebral metabolism to maintain or increase the magnitude of the temperature gradient between the brain and the patient's body core.

10. The method of claim 9, wherein the step of selectively controlling cerebral metabolism comprises administering an agent which controls cerebral metabolism.

11. The method of claim 1, comprising placing an air diffusing coverlet around a patient's head, the coverlet having a porous inner layer arranged to disperse the cooled air around the head.

12. The method of claim 11, wherein the air diffusing coverlet is placed around the patient's head such that an air space is maintained between the air diffusing coverlet and the patient's head.

13. The method of claim 12, wherein the air space ranges from 1–3 inches.

14. The method of claim 11, wherein the air diffusing coverlet includes one or more transparent windows, the method further comprising the step of visually monitoring selected areas of the patient's head to detect thermal injuries arising from the cold air being dispersed around the patient's head.

15. The method of claim 11, wherein the coverlet has an air diffusing neck collar capable of surrounding, and dispersing cooled air about, the patient's neck.

16. The method of claim 11, further comprising the step of placing a cooling head cushion under the patient's head to additionally cool the brain.

17. The method of claim 11, further comprising the step of utilizing an oral pharyngeal cooling device to additionally cool the brain.

18. The method of claim 11, further comprising the step of placing a cool water misting device around the patient's head to additionally cool the brain.

19. The method of claim 11, further comprising the step of placing a network of capillaries around the patient's head and circulating chilled liquid through the capillaries to additionally cool the brain.

20. The method of claim 1, wherein the brain temperature is reduced sufficiently to reduce the incidence of post-operative neurologic deficits in a patient at risk of suffering such deficits.

21. The method of claim 1, wherein said method is performed while rewarming the patient from hypothermic cardiopulmonary bypass, the brain temperature being thereby sufficiently reduced to reduce the incidence of post-operative neurologic deficits from said rewarming.

22. A method for lowering brain temperature independent of core temperature in a patient, comprising the steps of:
   selectively providing cooled air to the patient's head, and
   dispersing the cooled air about the head resulting in convective cooling of the brain, while
   selectively controlling cerebral blood flow to maintain or increase the magnitude of the temperature gradient between the brain and the patient's body core.

23. The method of claim 22, wherein the step of selectively controlling cerebral blood flow comprises administering an agent which controls cerebral blood flow.

24. The method of claim 23, wherein the agent comprises a cerebral vasoconstrictor.

25. The method of claim 23, wherein the agent comprises a cerebral vasodilator.

26. The method of claim 22, wherein the step of selectively controlling cerebral blood flow comprises the technique of $CO_2$-mediated vasoconstriction.

27. The method of claim 22, wherein the step of selectively controlling cerebral blood flow comprises the technique of $CO_2$-mediated vasodilation.

28. A method for lowering brain temperature independent of core temperature in a patient, comprising the steps of:
   selectively providing cooled air to the patient's head, and
   dispersing the cooled air about the head resulting in convective cooling of the brain, while
   selectively controlling cerebral metabolism to maintain or increase the magnitude of the temperature gradient between the brain and the patient's body core.

29. The method of claim 28, wherein the step of selectively controlling cerebral metabolism comprises administering an agent which controls cerebral metabolism.

* * * * *